United States Patent [19]
von König et al.

[11] 4,397,942
[45] Aug. 9, 1983

[54] PHOTOGRAPHIC MATERIAL, PROCESS FOR THE PRODUCTION THEREOF, PROCESS FOR THE PRODUCTION OF PHOTOGRAPHIC IMAGES AND NEW COMPOUNDS

[75] Inventors: Anita von König, Krefeld; Franz Moll, Leverkusen; Hermann Oediger, Cologne, all of Del.X

[73] Assignee: Agfa-Gevaert Aktiengesellschaft, Leverkusen, Fed. Rep. of Germany

[21] Appl. No.: 314,180

[22] Filed: Oct. 23, 1981

[30] Foreign Application Priority Data

Oct. 30, 1980 [DE] Fed. Rep. of Germany ....... 3040910

[51] Int. Cl.³ .......................... G03C 1/06; G03C 1/28
[52] U.S. Cl. ..................................... 430/446; 430/569; 430/599; 430/613; 430/614
[58] Field of Search ............... 430/446, 564, 566, 569, 430/600, 605, 611, 613, 614, 623, 599

[56] References Cited
PUBLICATIONS hem. Absts. vol, 79, 1973, p. 497, 85626n Re: USSR, 367405.
hem. Absts., vol. 95, 1981, p. 324, 30218f Re: Germ. Offen 2939304.

*Primary Examiner*—M. F. Downey
*Attorney, Agent, or Firm*—Connolly and Hutz

[57] ABSTRACT

Compounds of the formula

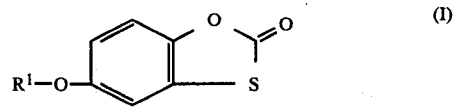

are suitable for the stabilization of the latent image in silver halide photographic materials.

8 Claims, No Drawings

PHOTOGRAPHIC MATERIAL, PROCESS FOR THE PRODUCTION THEREOF, PROCESS FOR THE PRODUCTION OF PHOTOGRAPHIC IMAGES AND NEW COMPOUNDS

This invention relates to a photographic material containing a latent image stabiliser, to a process for the production of this material, to a process for the production of photographic images and to new compounds.

It is known that the latent image nuclei of exposed silver halide emulsions are not stable in storage. This phenomenon is described, for example, in C. E. Kenneth Mees' book entitled "The Theory of the Photographic Process", 4th Edition, Macmillan Publishing Co., New York, 1977, pages 167 et seq.

Reformation of the latent image (fading) is usually reflected in the fact that an exposed material which was stored for development is less sensitive than a material which was stored after exposure. Although the reasons for fading have never been fully understood, it is assumed that it is initiated by substances in the emulsion, for example impurities or additives, which oxidise some of the silver of which the latent image consists. Fading is extremely troublesome in practice not only for recording materials which are usually stored for a prolonged period in exposed form before development, but also for copying materials which are not developed immediately after exposure. It is particularly when they are processed in roll form that copying materials are often developed a few days after exposure.

It is known that so-called "latent image stabilizers" may be added to photographic silver halide emulsions to stabilise the latent image nuclei. Latent image stabilisers are described, for example, in German Offenlegungsschrift Nos. 2,217,153; 1,107,508; 2,325,039 and 2,827,937; in German Auslegeschrift Nos. 1,199,612 and 1,173,339; in British Pat. Nos. 1,343,904; 1,412,294; 1,378,354; 1,386,630; 1,453,388 and 1,458,107, in British patent application No. 2,023,862 and in U.S. Pat. Nos. 3,386,831 and 3,881,935.

An object of the present invention is to achieve improved stabilisation of latent images.

Accordingly, the present invention relates to: (1) A photographic material of a layer support and at least one photosensitive silver halide emulsion layer applied thereto and optionally further layers, at least one layer containing a compound corresponding to the following general formula (I):

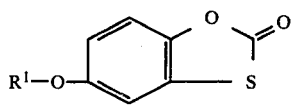

(I)

wherein $R^1$ represents hydrogen, an optionally substituted alkyl or acyl group or a 5- or 6-membered heterocycle.

$R^1$ preferably represents H, an alkyl group containing from 1 to 18 carbon atoms substituted by an alkoxy, cycloalkoxy, aralkoxy or aroxy group, an aliphatic acyl group particularly containing at most 20 carbon atoms, or an oxygen-containing heterocycle, particularly a tetrahydropyranyl radical.

Preferred substituents for an alkyl group are alkoxy radicals, particularly ethoxy radicals. A particularly preferred substituted alkyl radical is the ethoxy ethyl group.

Preferred acyl radicals are acetyl, propionyl, butyryl, pivaloyl, hexanoyl, lauroyl and stearoyl. One preferred substituted acyl radical corresponds to the following general formula (II):

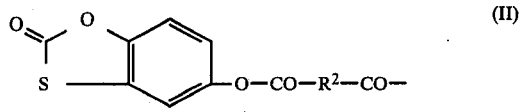

(II)

wherein $R^2$ represents a difunctional organic link, particularly alkylene, especially $C_1$-$C_{10}$ alkylene, arylene, especially phenylene, aralkylene, for example xylylene, or cycloalkylene, especially containing 5 or 6 carbon atoms.

(2) A process for the production of a photographic material comprising at least one silver halide emulsion layer by precipitating the silver halide in the presence of a protective colloid, optionally followed by physical and chemical ripening, and applying the casting solution obtained to a layer support, characterised in that compounds corresponding to general formula (I) are added before application.

(3) A process for the production of photographic images by image-wise exposure and development of the present material.

(4) New compounds corresponding to the following general formula:

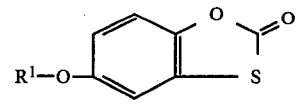

wherein $R^1$ represents a 5- or 6-membered heterocycle or a substituted acyl radical corresponding to the following general formula:

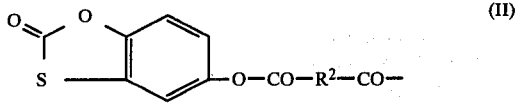

(II)

wherein $R^2$ represents a difunctional organic link, particularly alkylene, more particularly $C_1$-$C_{10}$ alkylene, arylene, especially phenylene, aralkylene, for example xylylene, cycloalkylene, especially containing 5 or 6 carbon atoms.

In one preferred embodiment, $R^1$ represents an oxygen containing heterocycle, particularly a tetrahydropyranyl radical.

The compounds corresponding to general formula (I) listed in Table (1) below have proved to be particularly suitable.

| No. | Compound |
| --- | --- |
| 1. | 5-hydroxy-2-oxo-1,3-benzoxathiol |
| 2. | 5-acetoxy-2-oxo-1,3-benzoxathiol |
| 3. | 5-propionyloxy-2-oxo-1,3-benzoxathiol |
| 4. | 5-butyryloxy-2-oxo-1,3-benzoxathiol |
| 5. | 5-pivaloyloxy-2-oxo-1,3-benzoxathiol |
| 6. | 5-hexanoyloxy-2-oxo-1,3-benzoxathiol |
| 7. | 5-lauroyloxy-2-oxo-1,3-benzoxathiol |
| 8. | 5-stearoyloxy-2-oxo-1,3-benzoxathiol |
| 9. | 5-(2-tetrahydropyranyloxy)-2-oxo-1,3-benzoxathiol |

| No. | Compound |
|---|---|
| 10. | 5-(2-ethoxyethyl)-oxy-2-oxo-1,3-benzoxathiol |

The phenyl radical condensed with the oxothiol ring in general formula (I) may carry additional substituents particularly short-chain alkyl and alkoxy radicals, or halogen, for example chlorine and bromine.

The compound according to the present invention may be produced by known methods. The production of compound No. 1 is described in German Auslegeschrift No. 1,225,198. The acyloxy compounds (compounds 2 to 8) may be produced from compound No. 1 with corresponding acid anhydrides and catalytic quantities of an acid, for example sulphuric acid or p-toluene sulphonic acid, or with corresponding acid halides in the presence of a base, for example pyridine or triethylamine. The production of compound No. 2 is described in J. Chem. Soc. 1952, page 2193.

The ethers (compounds 9 and 10) may be produced from compound No. 1 with the corresponding unsaturated ethers, for example dihydropyran, ethyl vinyl ether, in the presence of p-toluene sulphonic acid.

Compounds wherein $R^1$ represents a substituted acyl radical corresponding to general formula (II) may be produced in known manner from the 5-hydroxy-1,3-benzoxathiols and dicarboxylic acids with dicyclohexyl carbodiimide or dicarboxylic acid chlorides in the presence of pyridine.

The production of compound No. 9 is described in detail in the following, the other compounds being similarly obtained.

PRODUCTION OF COMPOUND NO. 9

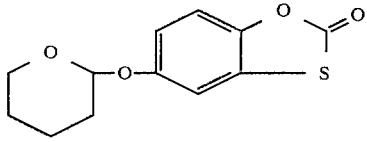

5-tetrahydropyranyloxy-2-oxo-1,3-benzoxathiol 8.4 parts, by weight, of 5-hydroxy-2-oxo-1,3-benzoxathiol are dispersed in 30 parts, by volume, of methylene chloride. First, 0.1 part, by weight, of p-toluene sulphonic acid and then at 0° C. 8.4 parts, by weight, of dihydropyran are added to the resulting dispersion. After stirring for 3 hours at 25° C., 0.5 part, by weight, of pyridine is added, the solution is filtered through a column of aluminium oxide and the above compound is obtained after the volatile constituents have drained off. Yield 10.5 parts, by weight, (78%). Melting point: 61°–63° C.

The compounds used in accordance with the present invention are eminently suitable for increasing the stability of the latent image nuclei in photosensitive photographic materials comprising at least one silver halide emulsion. The excellent stability of the latent image nuclei is achieved without detriment to the conventional photographic properties which, of course, are largely determined by the composition of the silver halide emulsion, even where the materials are stored for prolonged periods either at normal temperature or at elevated temperature in a heating stove.

The compounds used in accordance with the present invention are added to the photographic material in particular after physical ripening of the emulsion. The derivatives are preferably added in dissolved form to the photosensitive silver halide emulsion during or after chemical ripening or to the prepared casting solution. Suitable solvents are, in particular, lower aliphatic alcohols, tetrahydrofuran, acetone or mixtures thereof. The concentration of the compounds in the photographic materials may vary within wide limits. It depends upon the required effect, upon the type of reproduction process and upon the composition of the photographic material.

Where the compounds according to the present invention are used in a silver halide emulsion layer, quantities of from 10 to 5000 mg per mole of silver halide have proved to be suitable. Concentrations of from 50 to 1000 mg per mole of silver halide are particularly preferred.

The compounds used in accordance with the present invention may be employed for stabilising the latent image nuclei in conventional photosensitive materials which are suitable for the production of black-and-white images, for example black-and-white recording or copying materials or reversal materials. In addition, colour couplers may be present in the material without an adverse effect upon stabilisation.

Suitable protective colloids and binders for the silver halide emulsion layer are the conventional hydrophilic film-forming agents, for example proteins, particularly gelatin, alginic acid or derivatives thereof, such as esters, amides or salts, cellulose derivatives, such as carboxymethyl cellulose and cellulose sulphate, starch or derivatives thereof or hydrophilic synthetic binders, such as polyvinyl alcohol, partially hydrolysed polyvinyl acetate, polyvinyl pyrrolidone and others. The layers may also contain, in admixture with the hydrophilic binders, other synthetic binders in dissolved or dispersed form, such as homo- or co-polymers of acrylic or methacrylic acid derivatives thereof, such as esters, amides or nitriles, as well as vinyl polymers, such as vinyl esters or vinyl ethers.

The conventional layer supports may be used for the materials according to the present invention, for example supports of cellulose esters, such as cellulose acetate or cellulose acetobutyrate, polyesters, particularly polyethylene terephthalate, or polycarbonates, particularly based on bis-phenylolpropane. Paper supports originally containing water-impermeable polyolefin layers, for example of polyethylene or polypropylene, are also suitable, as are supports of glass or metal.

The conventional silver halide emulsions are suitable for the purposes of the present invention. The emulsions may contain, as silver halide, silver chloride, silver bromide or mixtures thereof, optionally with a small content of silver iodide of up to 10 mole percent.

The emulsions may also be chemically sensitised, for example by the addition during chemical ripening of sulphur-containing compounds, for example allyl isothiocyanate, allyl thiourea and sodium thiosulphate. Other suitable chemical sensitisers are reducing agents, for example the tin compounds described in Belgian Patent Nos. 493,464 and 568,687, also polyamines, such as diethylene triamine, or aminomethyl sulphinic acid derivatives, for example according to Belgian Patent No. 547,323. Suitable chemical sensitisers also include noble metals and compounds thereof, such as gold, platinum, palladium, iridium, ruthenium or rhodium. It is also possible to sensitise the emulsions with polyalkylene oxide derivatives, for example with polyethylene oxide having a molecular weight of from 1000 to 20,000, and also with condensation products of alkylene oxides and alcohols, aliphatic carboxylic acids, aliphatic amines, aliphatic diamines and amides.

The emulsions may also be optically sensitised, for example with the conventional polymethine dyes, such as neutrocyanines, basic or acid carbocyanines, rhodacyanines, hemicyanines, styryl dyes, oxanols and the like. Sensitisers of this type are described in F. M. Hamer's book entitled "The Cyanine Dyes and Related Compounds" (1964).

In combination with the stabilisers used in accordance with the present invention, the materials may contain other stabilisers, for example azaindenes, preferably tetra- or pentaazaindenes, particularly those substituted by hydroxyl or amino groups. Compounds of this type are described in the article by Birr in Z. Wiss. Phot. 47, 2-58 (1952). Other suitable stabilisers are inter alia heterocyclic mercapto compounds, for example phenylmercaptotetrazole, quaternary benzthiazole derivatives, benzotriazole and the like.

The layers of the photographic material may be hardened in the conventional way, for example with formaldehyde or with halogen-substituted aldehydes containing a carboxyl group, such as mucobromic acid, diketones, methane sulphonic acid esters, dialdehydes and the like. In addition, the photographic layers may be hardened with hardeners of the epoxide type, the heterocyclic ethylene imine type or the acryloyl type. It is also possible to harden the layers by the process according to German Offenlegungsschrift No. 2,218,009 to obtain photographic materials which are suitable for processing at high temperatures. The photographic layers or the colour photographic multilayer materials may also be hardened with hardeners of the diazine, triazine or 1,2-dihydroquinoline series. Examples of such hardeners are diazine derivatives containing alkyl or aryl sulphonyl groups, derivatives of hydrogenated diazines or triazines, such as 1,3,5-hexahydrotriazine, fluorine-substituted diazine derivatives, such as fluoropyrimidine, esters of disubstituted 1,2-dihydroquinoline or 1,2-dihydroisoquinoline-N-carboxylic acids. Other suitable hardeners are vinyl sulphonic acid hardeners, carbodiimide or carbamoyl hardeners of the type described, for example, in German Offenlegungsschrift Nos. 2,263,602; 2,225,230 and 1,808,685; in French Patent No. 1,491,807; in German Pat. No. 872,153 and in East German Pat. No. 7218. Other suitable hardeners are described, for example, in British Pat. No. 1,268,550.

The present invention may be used both for the production of black-and-white and also coloured photographic images. Coloured photographic images may be produced, for example, on the known principle of chromogenic development in the presence of colour couplers which react with the oxidation product of dye-producing p-phenylene diamine developers to form dyes.

The colour couplers may be added, for example, to the colour developer on the principle of the so-called "developing-in process". In one preferred embodiment, the photographic material itself contains the conventional colour couplers which are generally incorporated in the silver halide layers. Thus, the red-sensitive layer may contain, for example, a non-diffusing colour coupler for producing the cyan component of the colour image, generally a coupler of the phenol or α-naphthol type. The green-sensitive layer may contain, for example, at least one non-diffusing colour coupler for producing the magenta component of the colour image, colour couplers of the 5-pyrazolone of imidazolone type normally being used. The blue-sensitive layer may contain, for example, a non-diffusing colour coupler for producing the yellow component of the colour image, generally a colour coupler containing an open-chain ketomethylene group.

Colour couplers of this type are known in large numbers and are described in a number of patent specifications. Reference is made here, for example, to the article by W. Pelz entitled "Farbkuppler (Colour Couplers)" in "Mitteilungen aus den Forschungslaboratorien der Agfa, Leverkusen/München", Vol. III (1961) and K. Venkataraman in "The Chemistry of Synthetic Dyes", Vol 4, 341 to 387, Academic Press, 1971.

The non-diffusing colour couplers and dye-producing compounds are added to the photosensitive silver halide emulsions or other casting solutions by conventional known methods. Water-soluble or alkali-soluble compounds may be added to the emulsions in the form of aqueous solutions, optionally together with water-miscible organic solvents, such as ethanol, acetone or dimethyl formamide. When the non-diffusing colour couplers and dye-producing compounds are water- or alkali-insoluble compounds, they may be emulsified in known manner, for example by mixing a solution of these compounds in a low-boiling organic solvent directly with the silver halide emulsion or first with an aqueous gelatin solution, followed by removal of the organic solvent in the conventional way. An emulsion of the particular compound in gelatin obtained in this way is then mixed with the silver halide emulsion. So-called "coupler solvents" or "oil-formers" may be additionally used for incorporating hydrophobic compounds of this type by emulsification. Coupler solvents or oil-formers are generally relatively high boiling organic compounds which contain the non-diffusing colour couplers to be emulsified in the silver halide emulsions and development inhibitor releasing compounds in the form of oily droplets. In this connection, reference is made, for example, to U.S. Pat. Nos. 2,322,027; 2,533,514; 3,689,271; 3,764,336; and 3,765,897.

The photographic materials may be developed with conventional black-and-white developers, for example hydroquinone, pyrocatechol, p-methylaminophenol and 1-phenyl-3-pyrazolidone, and with colour developers, particularly of the p-phenylene diamine type, for example with N,N-dimethyl-p-phenylene diamine, 4-amino-3-methyl-N-ethyl-N-methoxyethyl aniline, 2-amino-5-diethylaminotoluene, N-butyl-N-ω-sulphobutyl-p-phenylene diamine, 2-amino-5-(N-ethyl-N-β-methane-sulphonamidoethylamino)-toluene, N-ethyl-N-β-hydroxyethyl-p-phenylene diamine, N,N-bis-(β-hydroxyethyl)-p-phenylene diamine and 2-amino-5-(N-ethyl-N-β-hydroxyethylamino)-toluene. Other suitable colour developers are described, for example in J. Amer. Chem. Soc. 73, 3100 (1951).

One particular advantage of the compounds used in accordance with the present invention is that stabilisation of the latent image nuclei is not dependent upon the simultaneous use of certain hardeners for the gelatin.

EXAMPLE 1

A high speed silver bromide iodide emulsion containing 6 mole percent of siliver iodide is prepared, flocculated and freed from the soluble salts in the conventional way. After redispersion, gelatin is added and the emulsion is ripened in known manner with sulphur and gold compounds. The emulsion has a silver (expressed as silver nitrate) gelatin ratio of 1:1 and contains 95 g of silver (expressed as silver nitrate) per kg.

The emulsion is divided into 5 equal portions before casting. The following ingredients are added to each of these portions (per kg) before casting: 200 mg of 4-hydroxy-6-methyl-1,3,3a,7-tetraazaindene in the form of a 1% aqueous alkaline solution; 600 mg of saponin in the form of a 10% solution in water; 10 ml of a 10% aqueous formalin solution; 10 ml of a 20% aqueous potassium bromide solution; and stabiliser to be used in accordance with the present invention in the form of a 1% alcoholic solution in the quantities indicated in Table 2 below.

The emulsions were then cast onto a cellulose acetate support in such a way that the silver coating (expressed as silver nitrate) amounted to 5.5 g per square meter. The samples were dried in the conventional way, exposed behind a grey step wedge in a sensitometer and, after the treatments at 20° C. shown in Table 2, were developed for 7 minutes and 16 minutes in a developer (I) of the following composition:

| | |
|---|---|
| sodium sulphite sicc. | 70 g |
| borax | 7.0 g |
| hydroquinone | 3.5 g |
| p-monomethylaminophenol sulphate | 3.5 g |
| sodium citrate | 7.0 g |
| potassium bromide | 0.4 g |
| made up with water to 1 liter. | |

The results of sensitometric evaluation are shown in Table 2 below.

TABLE 2

| Substance No. | Quantity added (mg) | (Fresh) | Speed after storage for 3 days at 60° C. | for 30 days at room temperature |
|---|---|---|---|---|
| — | — | standard | −5 | −6.5 |
| 1 | 10 | " | −1.4 | −2.1 |
| 1 | 30 | " | −1.3 | −1.5 |
| 2 | 30 | " | −2.5 | −2.5. |
| 2 | 60 | " | −2.1 | −1.8 |

In Table 2, speed is evaluated relative to the test taken as standard. Accordingly, differences in speed are quoted. An increase in this value by three units means a doubling of speed. Speed itself is determined at a density of 0.2 over fog.

We claim:

1. A photosensitive material for the production of photographic images containing at least one photosensitive silver halide emulsion layer and, optionally other layers, and having a soluble compound capable of increasing the stability of latent image nuclei in a quantity of from 10 to 5000 mg per mole of silver halide, wherein said soluble compound corresponds to the following formula

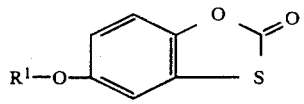

wherein $R^1$ represents hydrogen, an alkyl group, substituted alkyl group, an acyl group, a substituted acyl group, or a 5- or 6-membered heterocycle.

2. A material as claimed in claim 1, wherein $R^1$ represents hydrogen, an alkyl group containing from 1 to 18 carbon atoms substituted by an alkoxy, cycloalkoxy, aralkoxy or aroxy group, an aliphatic acyl group containing at most 20 carbon atoms or an oxygen-containing heterocycle.

3. A material as claimed in claim 1, wherein $R^1$ represents hydrogen or an alkyl group substituted by an alkoxy group.

4. A material as claimed in claim 1, wherein at least 5-hydroxy-2-oxo-1,3-benzoxathiol or 5-acetoxy-2-oxo-1,3-benzoxathiol or 5-(2-tetrahydropyranyloxy)-2-oxo-1,3-benzoxathiol is present.

5. A material as claimed in claim 1, wherein $R^1$ represents an acetyl, propionyl, butyryl, pivaloyl, hexanoyl, lauroyl or stearyl group or a substituted acyl radical corresponding to the following general formula:

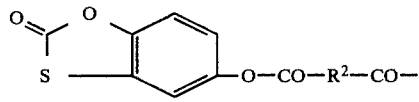

wherein $R^2$ is alkylene, arylene or aralkylene.

6. A process for the production of photosensitive photographic material having at least one layer containing silver halide comprising the steps of
reacting silver and halide salts to precipitate a silver halide,
ripening said silver halide in an emulsion,
incorporating in said emulsion a soluble stabilizing compound in a quantity of from 10 to 5000 mg per mole of silver halide according to the following formula

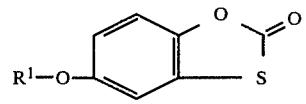

wherein $R^1$ represents hydrogen, an alkyl group, substituted alkyl group, an acyl group, a substituted acyl group, or a 5- or 6-membered heterocycle and applying the emulsion containing the stabilizer on a layer support.

7. In the process for the production of photosensitive photographic material as claimed in claim 6, the steps comprising
physical ripening of the emulsion and chemical ripening,
and incorporating said soluble stabilizing compound before chemical ripening.

8. A process for the production of photographic images in a photographic material including the steps of
imagewise exposing a photosensitive material containing at least one photosensitive silver halide emulsion layer having a soluble compound capable of increasing the stability of latent image nuclei in a quantity of from 10 to 5000 mg per mol of silver halide and corresponding to the following formula

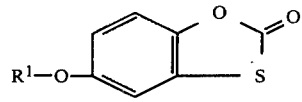

wherein $R^1$ represents hydrogen, an alkyl group, substituted alkyl group, an acyl group, a substituted acyl group, or a 5- or 6-membered heterocycle
developing the latent image of the exposed material in a photographic developer
and providing a developed image.

* * * * *